United States Patent [19]

Rock et al.

[11] 4,447,415
[45] May 8, 1984

[54] PLASMA-FREE MEDIUM FOR PLATELET STORAGE

[76] Inventors: Gail A. Rock, 270 Sandridge Rd., Rockcliffe Park, Canada, K1L 5A2; George A. Adams, 543 Broadview Ave., Ottawa, Canada, K2A 2L3

[21] Appl. No.: 449,762

[22] Filed: Dec. 14, 1982

[30] Foreign Application Priority Data

Nov. 1, 1982 [CA] Canada .................................. 414583

[51] Int. Cl.³ .............................................. A61K 35/14
[52] U.S. Cl. ........................................ 424/101; 435/1; 435/2
[58] Field of Search ...................... 435/1, 2; 424/101

[56] References Cited

U.S. PATENT DOCUMENTS 2,786,014  3/1957  Tullis ....................................... 435/1

OTHER PUBLICATIONS

Matsumoto–Chem. Abst. vol. 91 (1979) p. 136,650y.
Sivertsen–Chem. Abst. vol. 77 (1972) p. 73201r.

*Primary Examiner*—Sam Rosen
*Attorney, Agent, or Firm*—Holman & Stern

[57] ABSTRACT

Blood platelet concentrate in a plasma-free medium. Method for storage of blood platelets in a plasma-free medium which comprises centrifuging plasma to obtain a platelet pellet, removing the supernatant plasma, and resuspending the platelet pellet in a balanced salt medium. The balanced salt medium is an isotonic solution and may be selected from well known physiologically tolerable salt mediums. Additives to enhance platelet storage can be added to the salt medium.

28 Claims, No Drawings

PLASMA-FREE MEDIUM FOR PLATELET STORAGE

BACKGROUND OF THE INVENTION

This invention is concerned with a method for the storage of blood platelets in a plasma-free medium. Also described is a platelet concentrate obtained by this method.

Thrombocytopenia means low platelet counts in the circulatory system. Persons with this disease have a tendency to bleed as do hemophiliacs, except that the bleeding is usually from many small capillaries rather than from large vessels as in hemophilia. Such persons suffer small punctate hemorrhages throughout all the body tissues. The skin of such a person will exhibit many small, purplish blotches. Platelets are especially important for repair of minute breaks in capillaries and other small vessels. Platelets aglutinate to fill such ruptures without actually causing clots.

Normally, excessive bleeding does not occur until the number of platelets in the blood falls below a value of approximately 70,000 per cubic millimeter rather than the normal of 150,000 to 350,000.

At the present time, persons who have low platelet counts are supported by infusion of platelet concentrates. Platelet concentrates contain on average $6 \times 10^{10}$ platelets suspended in a volume of 50–60 ml of plasma. Larger platelet concentrates can be obtained using apheresis machinery, in which case the concentration is in the range of $4 \times 10^{11}$ and the plasma volume may reach 200–300 ml. Platelet concentrates can be kept for 3, 5 or even 7 days, depending on the type of bag and mode of rotation used.

There are generally speaking two types of blood collection and storage bags available. One type permits storage of platelets in plasma for up to 3 days while another type permits storage of platelets in plasma for up to 5 days and sometimes up to 7 days. The latter type is generally used for research purposes. In addition it should be noted that platelet storage bags must not contain the plasticizer di-2-ethyl-hexylphthalate and they should be highly permeable. While stored, all bags are subjected to rotation on a continuous basis which can be rotational about a transverse axis or horizontal and reciprocal or horizontal and circular.

SUMMARY OF THE INVENTION

The present inventors have developed a method whereby platelets can be stored in a medium other than plasma while still retaining the functional characteristics of platelets stored in plasma. The technique involves centrifugation of the plasma to obtain a platelet pellet, removal of the supernatant plasma, and subsequent resuspension of the platelet pellet in a balanced salt medium.

Thus, the present invention provides a method for the preparation of a platelet concentrate which comprises centrifuging plasma to obtain a platelet pellet, removing supernatant plasma and resuspending the platelet pellet in a balanced salt medium.

The plasma can be derived from freshly collected whole blood or may be collected using apheresis machinery, i.e. apheresis platelets. The blood or plasma is preferably collected from humans.

The balanced salt medium or isotonic solution is designed to provide the basic nutrients required for platelet support during storage and, as well, to enhance the environment above that obtained under plasma (physiological) conditions. More specifically, the isotonic solution or balanced salt medium comprises a conventional, physiologically tolerable isotonic solution to which various additional additives may be added to enhance platelet stability.

Examples of conventional balanced salt mediums or isotonic solutions which can be used for this purpose are Spinner salt solution (Eagle H, Science, 130:432 (1959)), Tyrode's (Tyrode, M.V., Arch. Intern. Pharmacodyn., 20:205 (1910)), Seligmann balanced salt solution (formula below), Earle's balanced salt solutions (Natl. Cancer. Inst. 4:167 (1943)), Dulbecco's phosphate buffered saline (J. Exp. Med., 98:167 (1954)), Hanks' balanced salt solutions (Proc. Soc. Exp. Biol. Med., 71:196 (1949)), modification-National Institutes of Health) Gey's balanced salt solutions (Amer. J. of Cancer, 27:55 (1936)), Puck's saline (Puck, T. T., Cieciura, S. J. and Robinson, A. J. Exp. Med., 108:945 (1958)).

The formula for Seligmann balanced salt solution is as follows:

| Component | mg/L |
| --- | --- |
| NaCl | 7650.00 |
| KCl | 200.00 |
| NaCO$_2$.CH$_3$ | 1500.00 |
| NaH$_2$PO$_4$.H$_2$O | 50.00 |
| KH$_2$PO$_4$ | 100.00 |
| D-Glucose | 1000.00 |
| NaHCO$_3$ | 700.00 |
| Ascorbic Acid | 3.00 |

There are several advantages to using a balanced salt solution in place of plasma and these are as follows. The plasma can be recovered and can be used for other purposes involving protein fractionation or transfusion to patients. Plasma is an expensive commodity and generally in short supply. Replacement of the plasma as a supernatant for platelet storage would result in considerable saving of plasma (estimated 14,000 liters in Canada alone in 1982) throughout the world.

Another advantage is the possibility of enhancing the storage environment above that generally found for plasma. Platelets are collected into an anticoagulant solution whose pH and biochemical constituents are chosen to enhance red cell preservation and which therefore may not be of optimal composition for platelet storage.

Besides the economic advantages, there are considerable theoretical medical advantages to removal of plasma and resuspension of platelets in a plasma free medium:

i. Removal of plasma components that are potentially harmful to platelets such as glycolytic and proteolytic enzymes that remove membrane glycoproteins and thus cause premature clearance from the circulation;

ii. Reduce the risk of exposure to infectious agents;

iii. Reduced risk of immediate and delayed allergic responses of recipients;

iv. Greater control over environmental conditions, especially pH, ion concentration and volume;

v. Reduced variations in platelet concentrates that would enhance the confidence of physicians in platelet concentrates perhaps leading to therapeutic regimes requiring fewer platelet concentrates per treatment; and vi. The addition of agents to the storage medium may further improve platelet function after storage or prolong the storage life of platelets.

The agents which can be added to the storage medium can include one or more of the following. Nutrients may be added to the medium, and may be selected from fructose and other sugars, adenine or acetyl CoA. These nutrients are substrates for the glycolytic or proteolytic enzymes on the platelet surface and prevent these enzymes from altering the platelet surface.

Another approach is to inhibit the above and other enzymes with reversible inhibitors that are diluted upon infusion into the circulatory system and hence no longer inhibitory. Examples of these compounds are indomethacin, quinacrine or vitamin E, all of which inhibit platelet activation during storage and perhaps increase storage life.

Yet another method to control platelet activation during storage is to raise cyclic adenosine monophosphate with exogenous prostaglandins $E_1$, $D_2$ or $I_2$ which again have a short half-life in vivo and reversible effects on platelets.

Finally, the artificial medium can be buffered by addition to the medium of a number of agents all of which can safely be infused into patients. These include phosphate and the amino acids: histidine, cysteine, tyrosine, lysine or arginine. These amino acids have the ability to buffer at an alkaline pH of 9 while phosphate precipitates at this pH.

Thus, in summary the isotonic solution may contain nutrients to improve the storage life of the platelets, reversible inhibitors for platelet activation, substances to raise cyclic adenosine monophosphate levels and which have reversible effects on platelets, and buffering agents which can be safely infused into patients. Generally these additives are used in physiological salt concentrations.

By the present method, the storage of platelet concentrates in a plasma free medium can be effected for at least 72 hours and results can be obtained which are similar to or better than those currently found using standard conditions of storage in plasma.

In another aspect, this invention provides a platelet concentrate in a plasma-free medium, which medium is a balanced salt medium which is an isotonic solution. The solution may be modified with the previously described agents. The present platelet concentrates can be stored for the same amount of time as presently available plasma concentrates can be stored. Further the platelet concentrates in the non-plasma medium are about the same as for the plasma medium, that is, about $10^9$ ml or $10^{12}$/L.

DETAILED DESCRIPTION OF THE INVENTION

The following examples are used to illustrate the present invention. All parts and percentages are by weight unless otherwise specified.

Two series of experiments were carried out to show the effects of storing platelets in a non-plasma medium. The first series (A) uses extraction and a washing step to remove plasma from platelets prior to final suspension in a Tyrode's solution. The second series (B) uses only extraction of plasma and final suspension in a modified Tyrode's solution containing either extra phosphate buffer or histidine buffer.

EXAMPLE 1

Series A

Method:

Preparation of Platelet Concentrates: Platelet concentrates were prepared by acidification of a pool of platelet-rich plasma using 35 ml acid-citrate-dextrose anticoagulant to 230 ml of platelet-rich plasma, to yield a final pH of 6.4. This lower pH allows immediate resuspension of platelets concentrated by the normal centrifugation procedure of 3000 g for 5.5 minutes. The plasma was extracted and the platelets resuspended in a washing solution containing 0.5 mM EDTA in calcium and magnesium-free Tyrode's buffer, pH 6.4. After centrifugation at 3000 g for 5.5 minutes and extraction of supernatant, the platelets were resuspended in (Citrate-Phosphate-Dextrose anticoagulant) CPD Tyrode's solution or CPD-plasma at a final volume of 60 ml in Pl-146 (plastic) bags (a trademark of Fenwall Company, Deerfield, Ill. 60015). The composition of the CPD-Tyrode's balanced salt solution is given in Table 1. These concentrates were stored at 22° C. in a horizontal shaker for testing after 3 days.

Platelet Aggregation: Aliquots from the platelet concentrates were diluted in pooled plasma containing CPD to a final concentration of $3 \times 10^8$ platelets/$\mu$l. After incubating for one hour at 37° the platelet suspensions were aggregated by addition of one stimulus or simultaneous addition of pairs of stimuli. The stimuli and concentrations used were adenosine diphosphate (ADP) at $10^{-5}$ M, epinephrine at $5 \times 10^{-5}$ M, collagen at 2.4 $\mu$g/ml, arachidonic acid at $10^{-4}$ M, and calcium ionophore A23187 at $5 \times 10^{-6}$ M. All these are final concentrations in the platelet suspensions.

Results:

The results for the platelets washed and resuspended in CPD-Tyrode's (Table 2), and CPD-plasma (Table 3) and for unwashed normal platelet concentrates (Table 4) are presented. The reported values are means and standard errors of at least three determinations except for those aggregations using arachidonate. The platelets stored in CPD-Tyrode's had slightly reduced aggregation responses when compared to the two control preparations stored in CPD-plasma. All three preparations lost the ability to aggregate to collagen, epinephrine or ADP while retaining aggregation response to pairs of stimuli or ionophore. The response of all three preparations were identical when tested before storage, indicating the washing procedure did not acutely alter the platelets (data not shown).

EXAMPLE 2

Series B

Method:

Preparation of Platelet Concentrates: Platelet concentrates were prepared by the normal centrifugation procedure of 3000 g for 5.5 minutes (no ACD was added). The plasma was extracted and the platelets resuspended in CPD-Tyrode's-phosphate solution, CPD-Tyrode's-Histidine (see Table 1 for recipes) or CPD-plasma at a final volume of 60 ml in PL 145 bags. These concentrates were stored at 22° C. in a horizontal shaker for testing after 3 days.

Platelet Aggregation: All aggregations were performed as in Series A.

Results:

The results for the platelets washed and resuspended in CPD-Tyrode's-phosphate (Table 5), and CPD-Tyrode's-Histidine (Table 6) and for unwashed normal platelet concentrates (Table 4) are presented and show values equal to or better than for platelets stored in the usual way in plasma. The reported values are means and standard errors of at least three determinations except for those aggregations using arachidonate. There was no difference between the platelets stored in CPD-Tyrode's-Histidine, CPD-Tyrode's-phosphate and the preparations stored in CPD-plasma. As in Series A, all three preparations lost the ability to aggregate to collagen, epinephrine or ADP while retaining aggregation response to pairs to stimuli or ionophore. The responses of all three preparations were identical when tested before storage, indicating the washing procedure did not significantly alter the platelets (data not shown).

TABLE 1
Composition of Some Artificial Mediums Used

|  | CPD-Tyrode's | CPD-Tyrode's-Phosphate | CPD-Tyrode's-Histidine |
|---|---|---|---|
| NaCl | 120 mM | 102 mM | 102 mM |
| KCl | 2.4 mM | 2.4 mM | 2.4 mM |
| NaHCO$_3$ | 22.0 mM | 10.0 mM | 10.0 mM |
| NaH$_2$PO$_4$ | 0.4 mM | 22.0 mM | — |
| CaCl$_2$ | 1.8 mM | 1.8 mM | 1.8 mM |
| MgCl$_2$ | 0.9 mM | 0.9 mM | 0.9 mM |
| Glucose | 22.0 mM | 22.0 mM | 22.0 mM |
| Citrate | 1.0 mM | 1.9 mM | 1.9 mM |
| Trisodium Citrate | 10.8 mM | 10.8 mM | 10.8 mM |
| Na$_2$HPO$_4$ | 1.9 mM | 1.9 mM | — |
| Histidine | — | — | 22.0 mM |
| pH | 7.4 mM | 7.4 mM | 7.4 mM |
| Osmolarity | 298 mOsm | 303 mOsm | 313 mOsm |

TABLE 2
Percent Platelet Aggregation After Storage of Washed Platelets at 22° C. for 72 hours in CPD-Tyrode's.

| Second Stimulus | First Stimulus |  |  |  |  |
|---|---|---|---|---|---|
|  | Saline | ADP | Epinephrine | Collagen | Arachidonate |
| Saline | 0 |  |  |  |  |
| ADP | 5(2)* |  |  |  |  |
| Epinephrine | 2(3) | 24(8) |  |  |  |
| Collagen | 1(2) | 26(2) | 22(18) |  |  |
| Arachidonate | 18(5) | — | 34 | — |  |
| Ionophore | 31(8) | 29(8) | 27(7) | 31(9) | — |

*mean (S.E.) of at least 3 determinations except for aggregations using arachidonate

TABLE 3
Percent Platelet Aggregation After Storage of Washed Platelets at 22° C. for 72 hours in CPD-Plasma.

| Second Stimulus | First Stimulus |  |  |  |  |
|---|---|---|---|---|---|
|  | Saline | ADP | Epinephrine | Collagen | Arachidonate |
| Saline | 0 |  |  |  |  |
| ADP | 8(5)* |  |  |  |  |
| Epinephrine | 1(1) | 40(4) |  |  |  |
| Collagen | 2(2) | 43(3) | 47(6) |  |  |
| Arachidonate | 21(2) | 48 | 46 | — |  |
| Ionophore | 40(2) | 45(6) | 40(4) | 47(10) | 46 |

*mean (S.E.) of at least 3 determinations except for aggregations using arachidonate

TABLE 4
Percent Platelet Aggregation After Storage of Unwashed Platelets at 22° C. for 72 hours in CPD-Plasma

| Second Stimulus | First Stimulus |  |  |  |  |
|---|---|---|---|---|---|
|  | Saline | ADP | Epinephrine | Collagen | Arachidonate |
| Saline | 0 |  |  |  |  |
| ADP | 14(5)* |  |  |  |  |
| Epinephrine | 0(1) | 40(2) |  |  |  |
| Collagen | 2(1) | 43(2) | 41(2) |  |  |
| Arachidonate | 27(3) | 44(2) | 43(5) | — |  |
| Ionophore | 47(5) | 46(2) | 39(2) | 46(2) | 44 |

*mean (S.E.) of at least 7 determinations except for aggregations using arachidonate which are means of 3 determinations.

TABLE 5
Percent Platelet Aggregation After Storage of Washed Platelets at 22° C. for 72 hours in CPD-Tyrode's-Phosphate.

| Second Stimulus | First Stimulus |  |  |  |  |
|---|---|---|---|---|---|
|  | Saline | ADP | Epinephrine | Collagen | Arachidonate |
| Saline | 0 |  |  |  |  |
| ADP | 7 |  |  |  |  |
| Epinephrine | 0 | 38 |  |  |  |
| Collagen | 2 | 47 | 41 |  |  |
| Arachidonate | 28 | 40 | 39 | 38* |  |
| Ionophore | 40 | 45 | 42 | 46 | 38* |

TABLE 6
Percent Platelet Aggregation After Storage of Washed Platelets at 22° C. for 72 Hours in CPD-Tyrode's-Histidine.

| Second Stimulus | First Stimulus |  |  |  |  |
|---|---|---|---|---|---|
|  | Saline | ADP | Epinephrine | Collagen | Arachidonate |
| Saline | 0 |  |  |  |  |
| ADP | 11 |  |  |  |  |
| Epinephrine | 1 | 35 |  |  |  |
| Collagen | 5 | 43 | 33 |  |  |
| Arachidonate | 24* | 42* | 38* | 33* |  |
| Ionophore A23187 | + | 48 | 37 | 43 | 30* |

*mean (S.E) of at least 3 determinations except for aggregation using arachidonate
+ 2 experiments gave no aggregation with ionophore A23187 while one gave 36% aggregation. Normal platelet aggregation to ionophore A23187 were found in CPD-Tyrode's-Phosphate.

The embodiments of the invention in which an exclusive property or privilege is claimed are defined as follows:

1. A method for the preparation of a blood platelet concentrate for administration to animals which comprises
    centrifuging plasma to obtain a platelet pellet,
    removing the supernatant plasma, and
    resuspending the platelet pellet in a medium consisting essentially of: a balanced, physiologically compatible, saline solution; an anticoagulant; and one or more additives to enhance stability of the platelets selected from (a) nutrients to improve the storage life of the platelets, (b) reversible inhibitors for platelet activation, (c) substances to raise cyclic adenosine monophosphate levels which have reversible effects on platelets, and (d) buffering agents which are physiologically compatible.

2. A method as claimed in claim 1 wherein the nutrients are selected from fructose, adenine or acetyl CoA.

3. A method as claimed in claim 1 wherein the reversible inhibitors for platelet activation are selected from indomethacin, quinacrine or vitamin E.

4. A method as claimed in claim 1 wherein the substances to raise cyclic adenosine monophosphate levels are selected from prostaglandins $E_1$, $D_2$ or $I_2$.

5. A method as claimed in claim 1 wherein the buffering agents are selected from phosphate or amino acids.

6. A method as claimed in claim 5 wherein the amino acids are selected from histidine, cysteine, tyrosine, lysine or arginine.

7. A method as claimed in claim 1 wherein the balanced salt medium is selected from Spinner salt solution, Tyrode's solution, Seligmann's balanced salt solution, Earle's balanced salt solutions, Dulbecco's phosphate buffered saline, Hank's balanced salt solutions, Gey's balanced salt solutions or Puck's saline.

8. A method as claimed in claim 1 wherein the balanced salt medium is a Tyrode's solution.

9. A method as claimed in claim 6 wherein the Tyrode's solution contains a phosphate buffer or a histidine buffer.

10. A method as claimed in claim 6 wherein extraction and a washing step is used to remove plasma from platelets prior to final suspension in the Tyrode's solution.

11. A method as claimed in claim 7 wherein extraction is used to remove plasma from platelets prior to final suspension in the modified Tyrode's solution.

12. A method as claimed in claim 1 wherein the plasma is human plasma.

13. A method as claimed in claim 1 wherein the plasma is derived from freshly collected whole blood or by apheresis.

14. A method as claimed in claim 1 wherein the plasma is derived from freshly collected whole human blood or by apheresis on a human donor.

15. A method as claimed in claim 1 wherein the plasma is human plasma.

16. A method as claimed in claim 1 wherein the plasma is derived from freshly collected whole blood or by apheresis.

17. A method as claimed in claim 1 wherein the plasma is derived from freshly collected whole human blood or by apheresis on a human donor.

18. A platelet concentrate composition for administration to animals comprising blood platelets suspended in a medium consisting essentially of:

a balanced, physiologically compatible, saline solution;

an anticoagulant; and one or more additives to enhance stability of the platelets selected from (a) nutrients to improve the storage life of the platelets, (b) reversible inhibitors for platelet activation, (c) substances to raise cyclic adenosine monophosphate levels which have reversible effects on platelets, and (d) buffering agents which are physiologically compatible.

19. A platelet concentrate as claimed in claim 18 wherein the nutrients are selected from fructose, adenine or acetyl CoA.

20. A platelet concentrate as claimed in claim 18 wherein the reversible inhibitors for platelet activation are selected from indomethacin, quinacrine or vitamin E.

21. A platelet concentrate as claimed in claim 18 wherein the substances to raise cyclic adenosine monophosphate levels are selected from prostaglandins $E_1$, $D_2$ or $I_2$.

22. A platelet concentrate as claimed in claim 18 wherein the buffering agents are selected from phosphate or amino acids.

23. A platelet concentrate as claimed in claim 22, wherein the amino acids are selected from histidine, cysteine, tyrosine, lysine or arginine.

24. A platelet concentrate as claimed in claim 18, wherein the balanced salt medium is selected from Spinner salt solution, Tyrode's solution, Seligmann balanced salt solution, Earle's balanced salt solutions, Dulbecco's phosphate buffered saline, Hank's balanced salt solutions, Gey's balanced salt solutions or Puck's saline.

25. A platelet concentrate as claimed in claim 18 wherein the balanced salt medium is a Tyrode's solution.

26. A platelet concentrate as claimed in claim 25 wherein the Tyrode's solution contains a phosphate buffer or a histidine buffer.

27. A platelet concentrate as claimed in claim 18 wherein the plasma is human plasma.

28. A platelet concentrate as claimed in claim 18 wherein the human plasma is derived from freshly collected whole blood or by apheresis on a human donor.

* * * * *